United States Patent
Klees et al.

(10) Patent No.: US 7,950,264 B2
(45) Date of Patent: May 31, 2011

(54) DISPOSABLE MEASUREMENT ARRANGEMENT AND METHOD OF TESTING AND/OR CALIBRATING IT

(75) Inventors: Daniel Klees, Greenwood, IN (US); Joseph W. Schaffer, Greenwood, IN (US); Mike Yitref, Greenwood, IN (US)

(73) Assignee: Endress + Hauser Conducta Gesellschaft für Mess-und Regeltechnik mbH + Co. KG, Gerlingen (DE)

( * ) Notice: Subject to any disclaimer, the term of this patent is extended or adjusted under 35 U.S.C. 154(b) by 689 days.

(21) Appl. No.: 11/987,438

(22) Filed: Nov. 30, 2007

(65) Prior Publication Data

US 2009/0139298 A1 Jun. 4, 2009

(51) Int. Cl.
*G01N 21/00* (2006.01)
(52) U.S. Cl. ........................................................ 73/1.03
(58) Field of Classification Search .................... None
See application file for complete search history.

(56) References Cited

U.S. PATENT DOCUMENTS

| | | | | |
|---|---|---|---|---|
| 5,188,803 | A | * | 2/1993 | Hochberg ........................ 422/99 |
| 5,212,092 | A | * | 5/1993 | Jackson et al. .................. 436/11 |
| 5,339,671 | A | * | 8/1994 | Ahmad et al. ................. 73/1.02 |
| 5,902,246 | A | * | 5/1999 | McHenry et al. ............. 600/476 |

* cited by examiner

*Primary Examiner* — Robert R Raevis
(74) *Attorney, Agent, or Firm* — Bacon & Thomas, PLLC

(57) ABSTRACT

A measurement arrangement comprising a flexible disposable container and a disposable measurement probe for measuring an analytical property of a medium. The measurement probe is mounted on an inside wall of the disposable container and comprises a sensing element extending into the container, which is ready to use and which produces reliable measurement results. The disposable measurement arrangement comprises a closed capsule containing a buffer solution and a tether connecting said capsule to said probe. The container, the measurement probe, the capsule and the buffer solution are sterilized. The sensing element is inserted in the buffer solution during storage and the capsule is removed from the sensing element during measurement operation.

13 Claims, 4 Drawing Sheets

DISPOSABLE MEASUREMENT ARRANGEMENT AND METHOD OF TESTING AND/OR CALIBRATING IT

BACKGROUND AND SUMMARY OF THE INVENTION

The present invention concerns a disposable measurement arrangement comprising a disposable container and a disposable measurement probe for measuring an analytical property of a medium and a method of testing and/or calibrating this arrangement.

Such arrangements are widely used in various branches of industry for example in the Pharmaceutical Industry, in Biotechnology, as well as in Medicine. They are for example used as bioreactors in Life Science Industry.

There is a wide range of analytical properties that need to be measured or monitored in these application, including for example a pH value, an Oxygen content, an oxidation reduction potential or a content of a specific ion.

In these branches of industry very high standards of hygiene are required. These standards may vary slightly from country to country, but in general they require, that any surfaces of the measurement arrangement, which may come in contact with the product can be effectively cleaned and/or sterilized.

In conventional measurement arrangements of this type, e.g. in bioreactors, closed systems are used. They comprise stainless steel vessels and the measurement probes are inserted through the metal ports into the vessel. The closed system is sterilized by hot steam or chemicals for a period of time to assure that all living organisms are inactivated. The bioreactor is cooled, dried and charged for example with media, cells, nutrients and gasses. The bioreaction is then started. Since the measurement probe was sterilized with the initial sterilization cycle of the system, the sterilized probe is in contact with the bioreaction media through the sidewall of the bioreactor. Electronic signals from the measurement probe are used for example to precisely control the analytical property measured therewith.

In order to avoid the time and costs involved in cleaning and/or sterilizing the closed system these Industries prefer to use presterilized disposable measurement arrangements.

The main advantage of disposable measurement arrangements is, that cleaning and sterilization of the equipment is no longer necessary. Disposable presterilized systems can be kept on stock. This allows for a great flexibility and time efficiency, especially when production lines need to be set up, enlarged or scaled down frequently.

Today, there is a wide range of disposable flexible containers on the market. They are for example manufactured by companies such as HyClone, Logan, Utah, USA or Sartorius BBI Systems GmbH, Germany. Disposable single use containers usually comprise a large flexible bag with aseptic connections for the attachment of tubing. The empty disposable containers are typically sterilized with gamma radiation and delivered to the user. The user attaches sterile tubing to the container via the aseptic connections which allow the connection of presterilized components without breaching sterility of the components. The user then adds media, e.g. cells and nutrients, and runs the process. At the end of the process, the disposable container is emptied and discarded.

In order to measure analytical properties of a medium inside the container, it is possible, to install corresponding measurement probes inside the container and to sterilize the measurement probe together with the container using gamma radiation.

Measurement probes for measuring the analytical properties, like the ones listed above, usually comprise a sensitive sensing element, that needs to be hydrated before use, in order to perform accurate measurements. In particular, they comprise electrochemical cells, having sensitive electrodes, membranes or diaphragms, which need to be hydrated during storage. If they are not hydrated prior to measurement, the sensing element will need time to adapt when immersed into the fluid to be measured, until a chemical equilibrium is established.

Hydration of the sensing elements of such measurement probes can be performed by inserting the probe into a buffer solution. With respect to the above mentioned measurement arrangement, where the probe is already built into the disposable container, this cannot be done without breaching the sterility of the arrangement.

In the International Patent Application WO 2004/059286 a method is described wherein a pH probe is inserted in a buffer solution, gamma sterilized and packaged together with the buffer solution. In order to use such a hydrated probe in the measurement arrangement under consideration, the probe would need to be unpacked and taken out of the buffer solution prior to installing it inside the disposable container. Since this installation would most likely breach the sterility of the arrangement, the entire arrangement will need to be sterilized again. Consequently the probe would begin to dry up during sterilization. If the measurement arrangement is not used immediately after sterilization, the sensing element of the probe will dry up again during storage of the measurement arrangement.

In addition, it has not been possible to use buffer solutions to validate that the measurement probe is functional or to perform a calibration of the measurement probe after it has been installed and sterilized inside the disposable container. In conventional measurement arrangements, tests and/or calibration procedures using buffer solutions can only be performed prior to the insertion of the measurement probe into the disposable container or into conventional bioreactors.

It is an object of the invention to provide a measurement arrangement comprising a sterile disposable container and a sterile measurement probe for measuring an analytical property of a product, wherein said measurement arrangement is ready to use and produces reliable measurement results.

To this end the invention comprises a disposable measurement arrangement comprising:
  a flexible disposable plastic container,
  a disposable measurement probe for measuring an analytical property of a medium, mounted on an inside wall of said disposable container, comprising a sensing element extending into the container,
  a closed capsule containing a buffer solution, and
  a tether connecting said capsule to said probe, wherein
  said container, said measurement probe, said capsule and said buffer solution are sterilized;
  said sensing element is inserted in said buffer solution during storage, and
  said capsule is removed from the sensing element during measurement operation.

According to a preferred embodiment, the measurement probe is a pH probe, an Oxygen content measurement probe, a specific ion concentration measurement probe or an oxidation reduction potential measurement probe.

According to a preferred embodiment, the measurement arrangement further comprises
  at least one additional closed capsule containing a reference medium having a known analytical property, said additional capsule comprising means for allowing for said sensing element to be inserted into said reference medium; and means for attaching said additional capsule to said probe.

According to a preferred embodiment, said means for allowing for said sensing element to be inserted into said reference medium comprise a piercable membrane or a removable lid that is tethered to the assembly.

The invention further comprises a method of testing and/or calibrating a disposable measurement probe of a disposable measurement arrangement according to the invention, wherein said buffer solution has a known analytical property, said sensing element is inserted into said buffer solution during testing and/or calibration, said analytical property of said buffer solution is measured with said measurement probe, and said measured analytical property is compared to said known analytical property of said buffer solution.

According to a preferred embodiment of this method, an Off Set of the measurement probe is adjusted based on said comparison of said measured analytical property and said known analytical property of said buffer solution.

The invention further comprises a method of calibrating a disposable measurement probe of a disposable measurement arrangement according to the invention, wherein said measurement arrangement comprises at least two capsules, each containing a different reference medium having a known analytical property, and each comprising means for allowing for said sensing element of said measurement probe to be inserted into said reference medium during a calibration procedure; comprising the steps of consecutively inserting said sensing element of said measurement probe into each of the reference media, measuring said analytical property of each reference medium with the probe whilst said sensing element is inserted in said reference medium, and comparing said measured analytical properties to the known analytical properties of the reference media.

According to a preferred embodiment of the last mentioned method, an Off Set and a Span of said measurement probe is adjusted based on said comparisons of said measured analytical properties and said known analytical properties of said reference media.

The invention further comprises a method of calibrating a disposable measurement probe of a disposable measurement arrangement according to the invention, wherein said measurement probe is an Oxygen content measurement probe, and said disposable container contains at least a small amount of sterile air having a known Oxygen content, comprising the step of:

removing said sensing element of said probe from said capsule containing said buffer solution, exposing said sensing element of said probe to said sterile air, measuring an Oxygen content of said air with said measurement probe and comparing said measured Oxygen content to said known Oxygen content.

The invention further comprises a method of removing a capsule from the measurement probe or of mounting a capsule on said disposable measurement probe of said measurement arrangement according to the invention, wherein said capsule is manually grasped through the flexible container wall and pulled of or inserted onto the measurement probe.

According to a preferred embodiment of the invention, said capsule containing the buffer solution contains a sponge like material that is saturated with the buffer solution, and each additional capsule containing a reference medium contains a sponge like material that is saturated with the reference medium.

It is an advantage of the invention, that the calibration of the measurement probe can be validated on site utilizing the buffer solution and/or the reference media.

The invention and further advantages are explained in more detail using the figures of the drawing, in which two exemplary embodiment are shown. The same reference numerals refer to the same elements throughout the figures.

BRIEF DESCRIPTION OF THE DRAWING

FIG. 8 shows the arrangement shown in FIG. 6, wherein the measurement probe is inserted in the other additional capsule.

DETAILED DESCRIPTION OF THE DRAWINGS

Figure 1:
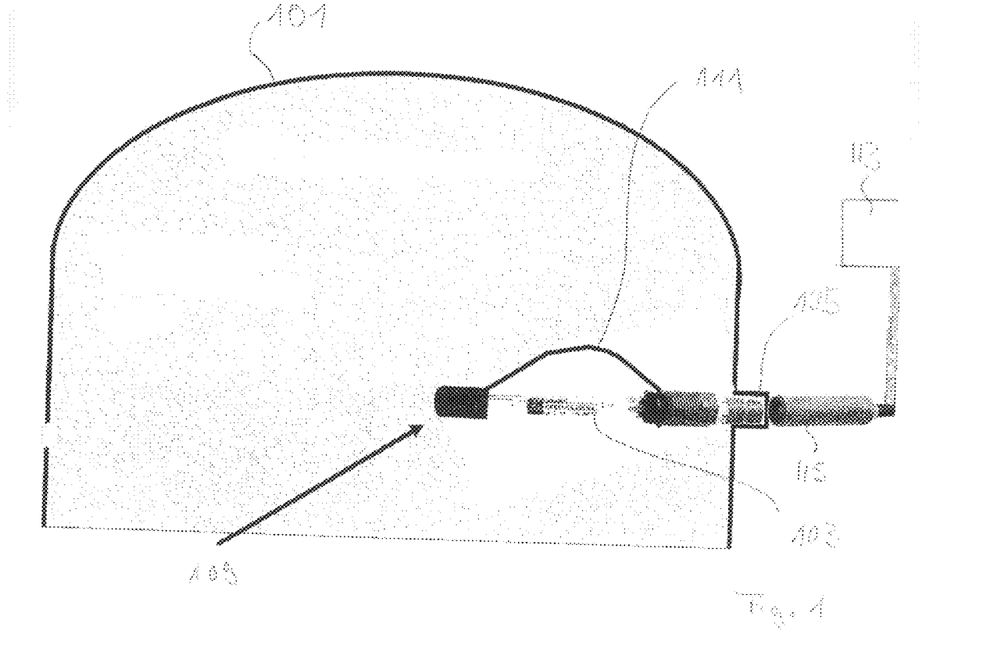
FIG. 1 shows a measurement arrangement according to the invention.

FIG. 1 shows a disposable measurement arrangement according to the invention. It comprises a flexible disposable plastic container 101. Today, there is a wide range of disposable flexible containers on the market. The are for example manufactured by companies such as HyClone, Logan, Utah, USA or Sartorius BBI Systems GmbH, Germany. Disposable single use containers usually comprise a large flexible bag with aseptic connections for the attachment of tubing, ports and fittings. Some companies, such as for example HyClone even offer custom configured designs.

The measurement arrangement further comprises a disposable measurement probe 103 for measuring an analytical property of a medium. The measurement probe 103 is for example a pH-probe for measuring a pH value of the medium, an Oxygen content measurement probe for measuring an Oxygen content of the medium, an oxidation reduction potential measurement probe for measuring an oxidation reduction potential of the medium or a specific ion concentration measurement probe for measuring a concentration of a specific ion in the medium.

Measurement probes 103 for measuring an analytical property of a medium are available on the market. In the embodiment shown in FIG. 1 a pH measurement probe sold by the applicant under the name Memosens is shown.

The measurement probe 103 is mounted on an inside wall of the flexible container 103. In the embodiment shown, a rear end of the elongated probe 103 is molded into a recess 105 in the container wall. Other ways of mounting the measurement probe 103 are known in the art. The rear end of the measurement probe 103 can for example be inserted in a corresponding fitting inside the container wall.

The measurement probe 103 comprises a sensing element 107, which extends into the container 101. In the embodiment shown, the sensing element 107 is located on an end of the probe 103 extending into the container 101.

During storage of the measurement probe 103 and of the measurement arrangement, the sensing element 107 is inserted in a closed capsule 109 containing a buffer solution, e.g. water. The buffer solution is chosen with respect to the type of measurement probe 103 used. Preferably the buffer solution consists of a material, which is Generally Recognized as Safe in accordance with the requirements listed in title 21 CFR177 issued by the U.S. Food and Drug Administration. The buffer solution keeps the sensing element 107 hydrated.

A tether 111 is permanently connecting the capsule 109 to the measurement probe 103. To this extend one end of the tether 111 is permanently attached to capsule 109. The other end of the tether 111 is permanently attached to the measurement probe 103. In the embodiment shown, the other end comprises a circular ring, which is inserted in a circular recess on an outside wall of the measurement probe 103.

Once the measurement arrangement is assembled, the entire arrangement including the container 101, the measurement probe 103, the capsule 109 and the buffer solution are sterilized, for example by gamma radiation. The entire measurement arrangement can now be packaged and sent to the customer or stored for later use. It is ready to use whenever it is needed. Since the buffer solution is sterilized inside the measurement arrangement, it does not have to contain preservatives. The sensing element 107 is kept hydrated until the measurement probe 103 is needed. This ensures, that the measurement probe 103 remains immediately functional. No time is needed, for the sensing element 107 to become hydrated in the process. Measurements with minimal drift can be immediately performed in the process.

Whenever the measurement arrangement is needed, it is set up on site and connected to the process it is needed for. A measurement electronic 113 is connected to the measurement probe 103 via an appropriate connector 115. During measurement operation, the measurement electronic 113 receives a measurement signal from the probe 103 and produces an output signal representing the measured value of the analytical property of the medium. Preferably, the connector 115 provides an inductive coupling between the measurement probe 103 and the measurement electronics 113, allowing for an inductive transmission of the measurement signal of the measurement probe 103. Preferably, the inductive coupling allows for digital communication and provides an energy supply for the measurement probe 103. Such an inductive coupling provides the advantage, that no opening needs to be provided on the respective section of the container wall. The inductive coupling can be mounted on the counter connector on the probe 103 which is covered by the container wall. Energy and signals are then exchanged through the unimpaired wall section separating the two, as indicated in FIG. 1. In this case, the corresponding wall section provides a sterile barrier between the measurement probe 103 and the connector 115.

Alternatively, measurement probes without conductive couplings can be used. Such probes can be connected to a measurement electronic outside the container, for example by a connecting cable, that is fed through the container wall.

Prior to the start of the measurement operation, the capsule 109 is removed from the sensing element 107. Preferably, the capsule 109 is removed by manually grasping it through the flexible container wall and pulling it of the measurement probe 103.

Figure 2:
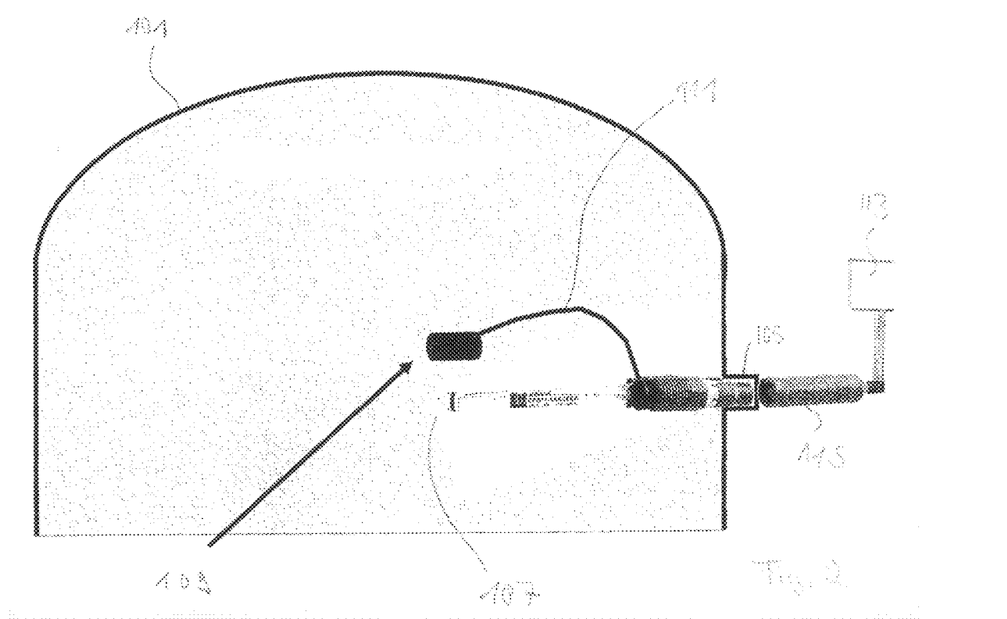
FIG. 2 shows the measurement arrangement shown in FIG. 1, wherein the capsule containing a buffer solution has been removed from the measurement probe.

After removal the capsule 109 is held inside the container 101 via the tether 111. This is shown in FIG. 2. It remains attached to the probe 103 throughout the entire use of the measurement arrangement. This prevents the capsule 109 from getting lodged e.g. in an outlet port of the container 101 or in other devices used inside the container 101 or connected to the container 101, for example valves, pumps, filters or other process devices.

Since the buffer solution is sterile and Generally Recognized as Safe according to FDA 21CFR177.xxx. it can remain inside the container 101 without adulteration issues. Preferably an inside chamber of the capsule 109 containing the buffer solution, is shaped to closely surround the sensing element 107. This ensures, that only very little amounts of the buffer solution are needed to hydrate the sensing element 107 prior to measurement. Preferably, the capsule 109 contains a sponge like material that is saturated with the buffer solution. This sponge like material keeps the buffer solution in close contact to the measuring probe 103. The material can for example be a synthetic sponge or a natural sponge.

Figure 3:
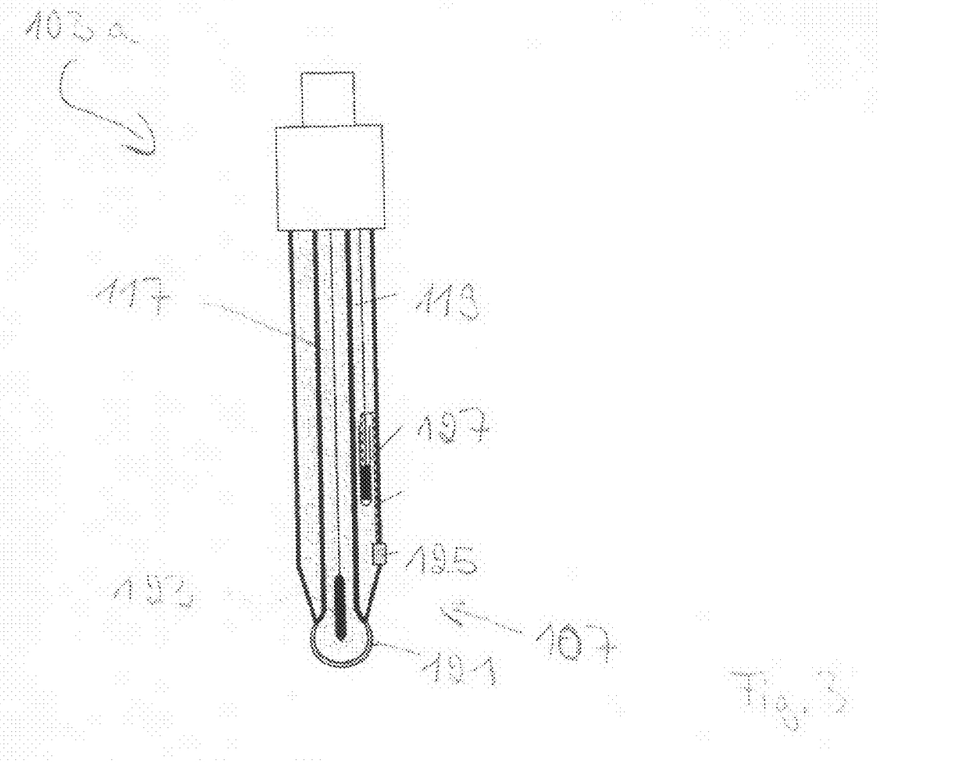
FIG. 3 shows a pH measurement probe.

According to one embodiment of the invention, the measurement probe 103 is a pH probe 103a. FIG. 3 shows an example of a pH measurement probe. Such probes are sold by the application and described in detail in a book titled: Wastewater measurement and control, first edition, published in 1992 by the Endress+ Hauser (International) Holding AG, Switzerland.

The measuring probe 103a comprises a measuring cell 117 and a reference cell 119. The measuring cell 117 comprises a tip 121 consisting of a material, that is sensitive to pH, that is, it generates an electric potential when it comes in contact with H+ ions. Such materials are for example special glasses. Inside, the measuring cell 117 is filled with a buffer solution and a measuring electrode 123 is inserted into the buffer solution inside the tip 121.

The reference cell 119 comprises a diaphragm 125 consisting of a material, that is insensitive to pH, e.g. ceramic. It is filled with a liquid or gelled electrolyte and a reference electrode 127 is inserted into the electrolyte near the diaphragm 125.

During measurement the pH-probe 103a is exposed to the medium to be measured inside the container 101 such that the tip 121 and the diaphragm 125 are immersed. The pH dependent electrical potential is taken via the measuring electrode 123 and measured against the potential derived via the reference electrode 127. The pH value to be measured is then determined based on Nernst's equation.

The sensing element 107 of this probe 103a, comprises the tip 121 and the diaphragm 125, and is kept hydrated by the buffer solution as long as sensing element 107 remains inside the capsule 109.

Preferably, a buffer solution having a known pH value is used. In this case, an initial calibration procedure can be performed prior to the measurement operation in the actual process. During this initial calibration procedure, the sensing element 107 remains inserted in the buffer solution and an initial measurement of the pH value of the buffer solution is performed with the measurement probe 103a. The measurement result is produced by the measurement electronics 113 and compared to the known pH value of the buffer solution. This one point calibration procedure can be applied, e.g. to test and/or verify that the measurement probe 103a is fully functional. In addition, the difference between the measured pH value and the known pH value can be used to adjust an Off Set of the measurement probe 103a.

Figure 4:
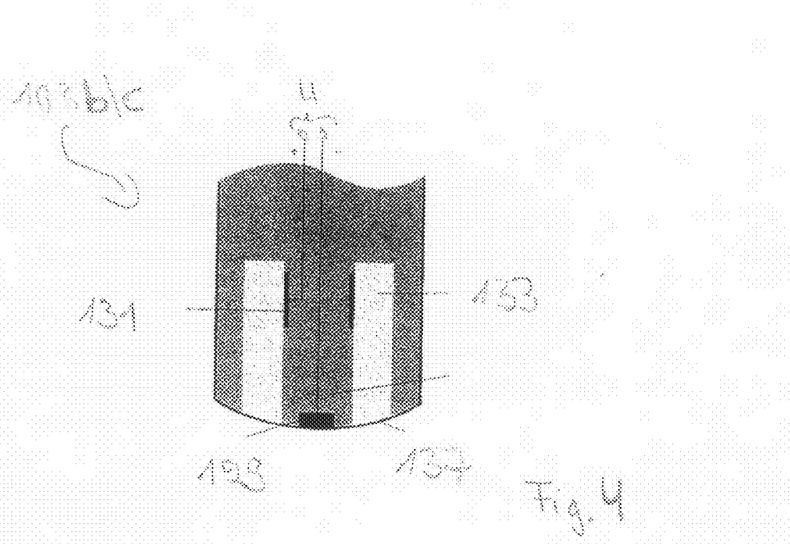
FIG. 4 shows an Oxygen content measurement probe or a specific ion contend measurement probe.

According to another embodiment of the invention, the measurement probe 103 is an Oxygen content measurement probe 103*b*. FIG. 4 shows an example of a measuring cell of an Oxygen content measurement probe 103*b*. It comprises a cathode 129, serving a measurement electrode and an anode 131 acting as ounter electrode and reference electrode. The cathode 129 is for example made of gold or platinum. The anode 131 is for example made of silver. Both electrodes are immersed in an electrolyte 133, for example potassium chloride (KCI). A membrane 137 is foreseen, separating the electrodes and the electrolyte 133 from the medium to be measured. A so called polarization voltage U is applied between the anode 131 and the cathode 129. If the probe 103*b* is immersed in a medium containing dissolved Oxygen, the Oxygen diffuses through the membrane 137. The Oxygen molecules that appear at the negative cathode 129 are reduced to hydroxide ions and an electrochemically equivalent amount of silver chloride is deposited on the anode. The cathode 129 gives off four electrons for every molecule of Oxygen, which are accepted by the silver anode 131. This causes a current, which is proportional to the Oxygen content of the medium to be measured.

Here the measurement cell, in particular its membrane 137 form the sensing element 107, that is kept hydrated by the buffer solution prior to measurement, in order to ensure drift free measurements.

Preferably, a buffer solution having a known Oxygen content is used. In this case, an initial calibration procedure can be performed prior to the measurement operation. During this initial calibration procedure, the sensing element 107 remains inserted in the buffer solution and an initial measurement of the Oxygen content value of the buffer solution is performed with the measurement probe 103*b*. The measurement result is produced by the measurement electronics 113 and compared to the known Oxygen content value of the buffer solution. This one point calibration procedure can applied, e.g. to test and/or verify that the measurement probe 103*b* is fully functional. In addition, the outcome of the comparison between the measured Oxygen content value and the known Oxygen content value can be used to adjust an Off Set of the measurement.

When an Oxygen content measurement probe 103*b* is used, it is very advantageous, to leave at least a small amount of air inside the container 101. The air is sterilized together with the container 101, the Oxygen content measurement probe 103*b* and the capsule 109 containing the buffer solution. Sterile air has a known content of Oxygen and can be used to perform an on site verification of the functionality of the probe 103*b* as well as a one point calibration of the probe 103*b* prior to measurement operation in the actual process. To this extend, the capsule 109 containing the buffer solution is removed from the Oxygen content measurement probe 103*b*. The sensitive element of the probe 103*b* is thus exposed to the sterile air inside the container 101 and the Oxygen content of the sterile air is measured with the measurement probe 103*b*. The measurement result is produced by the measurement electronics 113 and compared to the known Oxygen content value of the sterile air. This one point calibration procedure can applied, e.g. to test or verify that the measurement probe 103*b* is fully functional. In addition, the difference between the measured Oxygen content value and the known Oxygen content value of the sterile air can be used to adjust an Off Set of the measurement.

This method can be used either instead of the previously described method using a buffer solution with a known Oxygen content or in addition to it. If both methods are applied and the known Oxygen content of the buffer solution is different from the known Oxygen content of sterile air, a two point calibration can be performed, wherein the Measured Oxygen content of the buffer solution and the measured Oxygen content of the sterile air are measured with the probe 103*b* and compared to the known values. Offset and Span of the measurement are then adjusted according to the outcome of the measurements.

According to another embodiment of the invention, the measurement probe 103 is a specific ion content measurement probe 103*c*. The same measurement cell design, shown in FIG. 4, can be used in specific ion content measurement probes to measure a specific ion content of a medium, e.g. chloride, by using appropriate materials for the membrane 137, the electrodes and the electrolyte 133. For measuring chloride content, the cathode 129 is for example made of gold and the anode 131 is for example made of silver. The electrolyte 133 on the inside contains chloride ions and enables the growth of silver chloride on the anode 131. The membrane 137 separating the electrodes and the electrolyte 133 from the medium to be measured, is made of a porous material selectively permitting ion exchange of the specific ions to be measured between the electrolyte 133 inside the measurement cell and the medium being measured. A polarization voltage U is applied between the anode 131 and the cathode 129. If the probe 103*c* is immersed in a medium containing the specific ions, ions on the outside medium depolarize the measuring electrode, cathode 129, and so generate a current that is proportional to the specific ion concentration.

Figure 5:
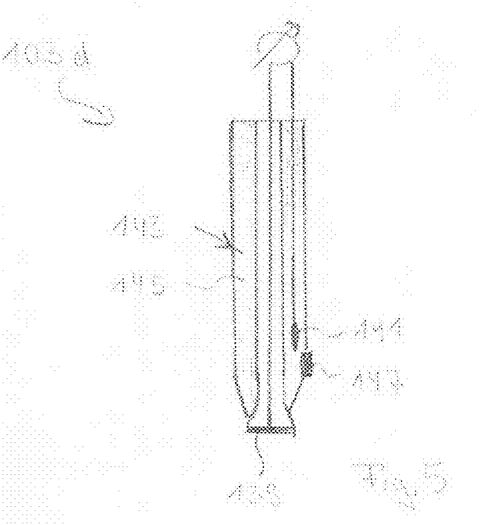
FIG. 5 shows a oxidation reduction potential measurement probe.

According to another embodiment of the invention, the measurement probe 103 is an oxidation reduction potential measurement probe 103*d*. FIG. 5 shows a schematic diagram of a measurement cell of such a probe comprising an inert noble metal measurement electrode 139 and a reference electrode 141. The reference electrode 141 is inserted into a reference cell 143, which is filled with an electrolyte 145 and comprises a diaphragm 147 permitting ion exchange between the electrolyte 145 and the medium to be measured. When the probe 103*d* is immersed in the medium to be measured a potential develops between the measurement electrode 139 and the reference electrode 141, which is a measure of the oxidation reduction potential of the medium.

Figure 6:
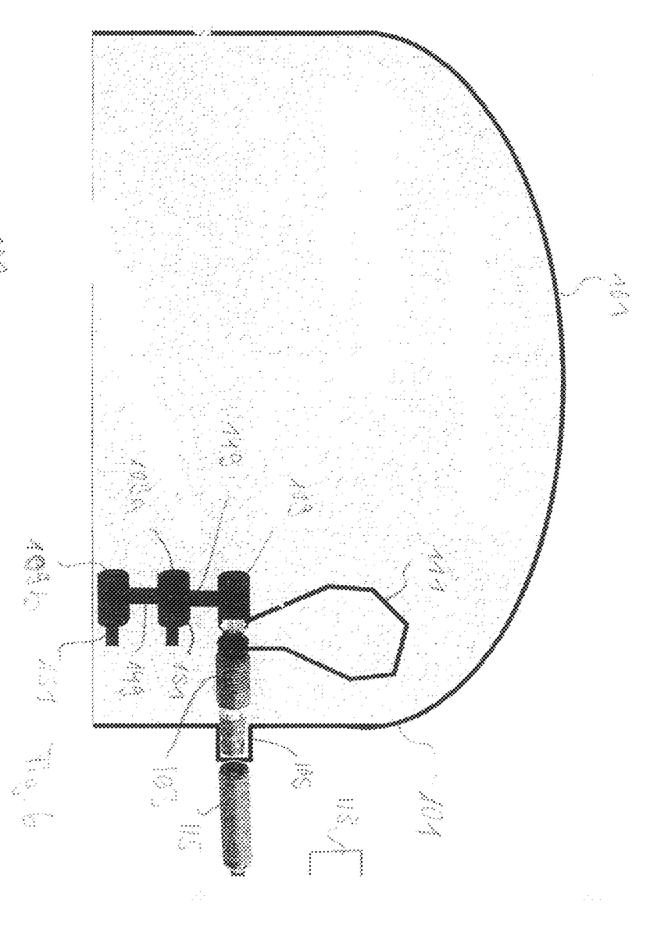
FIG. 6 shows a measurement arrangement comprising two additional capsules containing reference media.

Preferably, the measurement arrangement according to the invention comprises at least one additional closed capsule 109*a*, 109*b* each containing a reference medium having a known analytical property. FIG. 6 shows an embodiment comprising the capsule 109 containing the buffer solution and two additional capsules 109*a*, 109*b* each containing a different reference medium having a known analytical property. Means are foreseen for connecting each additional capsule 109*a*, 109*b* to the probe 103. In the embodiment shown, all three capsules 109, 109*a*, 109*b* are connected to each other by connecting elements 149. The entire group of capsules 109, 109*a*, 109*b* is connected to the probe 103 via the tether 111 which is attached to the capsule 109 containing the buffer solution and to the probe 103, in the same way as described with respect to the embodiment shown in FIGS. 1 and 2.

Each additional capsule 109*a*, 109*b* comprises means for allowing for the sensing element 107 of the measurement probe 103 to be inserted into the reference medium of the respective capsule 109*a*, 109*b*. These means are for example a piercable membrane 151 closing off the capsules 109*a*, 109*b*, as shown in the figures.

Alternatively a lid can be used. The lid is preferably permanently attached to the capsule via a hinge, tether or an other type of connector in order to ensure that the lid remains attached to the capsule and the probe when opened.

Preferably, the capsule 109*a*, 109*b* contain a sponge like material that is saturated with the respective reference medium. This sponge like material keeps the reference medium in close contact to the measuring probe 103 whilst the probe 103 is inserted.

The additional capsules 109a, 109b and the reference media contained therein are sterilized together with the container 101, the measurement probe 103 and the capsule 109 containing the buffer solution.

In this embodiment, the sensing element 107 of the measurement probe 103 is inserted in the capsule 109 containing the buffer solution during sterilization and later during storage. The buffer solution ensures that the sensing element 107 is kept hydrated during the entire storage time and thus ready to use whenever it is needed.

The arrangement is taken out of storage when needed and installed on site. During installation, the arrangement is connected to the process and the measurement electronic 113 is connected to the probe 103 via the connector 115. The functionality of the measurement probe 103 can now be tested as described above.

In addition, the measurement probe 103 can be calibrated on site, whilst it is already installed within the container 101 without breaching the sterility of the measurement arrangement or of the internal portion of the container 101.

To this extend the capsule 109 containing the buffer solution is manually grasped through the flexible container 101 wall and pulled of the measurement probe 103.

Figure 7:
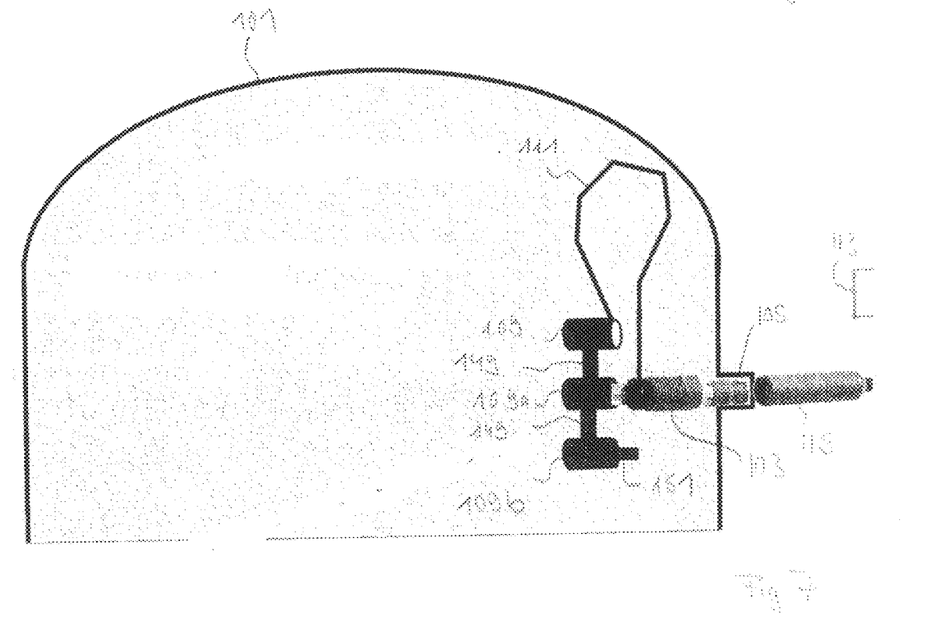
FIG. 7 shows the arrangement shown in FIG. 6, wherein the measurement probe is inserted in one of the additional capsules.

Then, one of the additional capsules, here capsule 109a, is manually grasped through the container 101 wall and inserted onto the measurement probe 103, as shown in FIG. 7, such that the sensing element 107 of the probe 103 is immersed in the reference medium contained in this capsule 109a. In a next step, the analytical property of this reference medium is measured with the measurement probe 103 and compared to the known value of this analytical property.

Next, the capsule 109a is manually grasped through the flexible container wall and pulled of the measurement probe 103, and the next capsule 109b is inserted onto the measurement probe 103, as shown in FIG. 8, such that the sensing element 107 of the probe 103 is inserted in the reference medium contained therein. Again, the analytical property of this reference medium is measured with the measurement probe 103 and compared to the known value of this analytical property.

Preferable, Offset and Span of the measurement are then adjusted according to the outcome of the measurements.

Obviously, it is possible to perform more advanced calibration procedures, by further increasing the number of capsules containing the different reference fluids, consecutively inserting the sensing element 107 of the measurement probe 103 into each of the reference media, measuring the analytical property of each reference medium with the probe 103 whilst the sensitive element 107 is inserted in the respective reference medium, and comparing the measured analytical properties to the known analytical properties of the reference media.

In addition, the buffer solution can be used as a reference medium for calibration purposes provided it has a known analytical property. In that case, it is sufficient to provide only one additional capsule containing a reference medium having a known analytical property to perform a two point calibration provided that the known analytical property of the reference medium is different from the known analytical property of the buffer solution.

| | |
|---|---|
| 101 | disposable container |
| 103 | measurement probe |
| 105 | recess |
| 107 | sensing element |
| 109 | capsule |
| 111 | tether |
| 113 | measurement electronic |
| 115 | connector |
| 117 | measuring cell |
| 119 | reference cell |
| 121 | tip |
| 123 | measuring electrode |
| 125 | diaphragm |
| 127 | reference electrode |
| 129 | cathode |
| 131 | anode |
| 133 | electrolyte |
| 135 | membrane |
| 137 | connecting elements |
| 139 | inert noble metal electrode |
| 141 | reference electrode |
| 143 | reference cell |
| 145 | electrolyte |
| 147 | diaphragm |
| 149 | connector |
| 151 | piercable membrane |

What is claimed is:

1. A disposable measurement arrangement comprising:
a flexible disposable plastic container,
a disposable measurement probe for measuring an analytical property of a medium, mounted on an inside wall of said disposable container, comprising a sensing element extending into said container;
a closed capsule containing a buffer solution; and
a tether connecting said capsule to said probe, wherein:
said container, said measurement probe, said capsule and said buffer solution are sterilized;
said sensing element is inserted in said buffer solution during storage; and
said capsule is removed from the sensing element during measurement operation.

2. A disposable measurement arrangement according to claim 1, wherein:
said capsule contains a sponge like material that is saturated with the buffer solution.

3. The disposable measurement arrangement according to claim 1, wherein:
said measurement probe is one of: a pH probe, an Oxygen content measurement probe, a specific ion concentration measurement probe and an oxidation reduction potential measurement probe.

4. The disposable measurement arrangement according to claim 1, further comprising:
at least one additional closed capsule containing a reference medium having a known analytical property, said additional capsule comprising means for allowing for said sensing element to be inserted into said reference medium; and
means for attaching said additional capsule to said probe.

5. A disposable measurement arrangement according to claim 4, wherein:
each additional capsule contains a sponge like material that is saturated with the reference medium.

6. The disposable measurement arrangement according to claim 4, wherein:
said means for allowing for said sensing element to be inserted into said reference medium comprises one of:

a piercable membrane and a removable lid that is tethered to the assembly.

7. A method of testing and/or calibrating a disposable measurement probe of a disposable measurement arrangement comprising:
a flexible disposable plastic container,
a disposable measurement probe for measuring an analytical property of a medium, mounted on an inside wall of said disposable container, comprising a sensing element extending into said container;
a closed capsule containing a buffer solution; and
a tether connecting said capsule to said probe, wherein:
said container, said measurement probe, said capsule and said buffer solution are sterilized;
said sensing element is inserted in said buffer solution during storage; and
said capsule is removed from the sensing element during measurement operation;
the method comprises the steps of:
providing a known analytical property for the buffer solution;
inserting the sensing element into the buffer solution during testing and/or calibration;
measuring the analytical property of the buffer solution with the measurement probe; and
comparing the measured analytical properties to the known analytical properties of the buffer solution.

8. The method of calibrating a disposable measurement probe of a disposable measurement arrangement according to claim 7, further comprising the steps of:
adjusting an Off Set of the measurement probe based on the comparison of the measured analytical property and the known analytical property of the buffer solution.

9. The method of calibrating a disposable measurement probe of a disposable measurement arrangement according to claim 7, wherein:
the measurement arrangement comprises at least two capsules, each containing a different reference medium having a known analytical property, and each comprising means for allowing for the sensing element of the measurement probe to be inserted into the reference medium during a calibration procedure, further comprising the steps of:
consecutively inserting the sensing element of the measurement probe into each of the reference media;
measuring the analytical property of each reference medium with the probe whilst the sensing element is inserted in the reference medium; and
comparing the measured analytical properties to the known analytical properties of the reference media.

10. The method of calibrating a disposable measurement probe of a disposable measurement arrangement according to claim 9, wherein:
an Off Set and a Span of the measurement probe is adjusted based on the comparisons of the measured analytical properties and the known analytical properties of the reference media.

11. The method of calibrating a disposable measurement probe of a disposable measurement arrangement according to claim 7, wherein:
said measurement probe is an Oxygen content measurement probe, and said disposable container contains at least a small amount of sterile air having a known Oxygen content, further comprising the steps of:
removing the sensing element of the probe from the capsule containing the buffer solution;
exposing the sensing element of said probe to the sterile air; and
measuring an Oxygen content of the air with the measurement probe and comparing the measured Oxygen content to the known Oxygen content.

12. A method of removing a capsule from a disposable measurement probe including: a flexible disposable plastic container, a disposable measurement probe for measuring an analytical property of a medium, mounted on an inside wall of said disposable container, comprising a sensing element extending into said container; a closed capsule containing a buffer solution; and a tether connecting said capsule to said probe, wherein: said container, said measurement probe, said capsule and said buffer solution are sterilized; said sensing element is inserted in said buffer solution during storage; said capsule is removed from the sensing element during measurement operation; said measurement probe is one of: a pH probe, an Oxygen content measurement probe, a specific ion concentration measurement probe and an oxidation reduction potential measurement probe, the method comprising the step of:
manually grasping said capsule through the flexible wall of the disposable container and pulling off of said capsule of said measurement probe.

13. A method of mounting an additional capsule on the disposable measurement probe of a measurement arrangement including:
a flexible disposable plastic container, said disposable measurement probe for measuring an analytical property of a medium, mounted on an inside wall of said disposable container, comprising a sensing element extending into said container; a closed capsule containing a buffer solution; and
a tether connecting said capsule to said probe, wherein:
said container, said measurement probe, said capsule and said buffer solution are sterilized;
said sensing element is inserted in said buffer solution during storage;
said capsule is removed from the sensing element during measurement operation;
said measurement probe is one of: a pH probe, an Oxygen content measurement probe, a specific ion concentration measurement probe and an oxidation reduction potential measurement probe;
at least one additional closed capsule containing a reference medium having a known analytical property, said additional capsule comprising means for allowing for said sensing element to be inserted into said reference medium; and
means for attaching said additional capsule to said probe, the method comprising the step of:
manually grasping said additional capsule through the flexible wall of the disposable container and inserting said additional capsule onto said measurement probe.

* * * * *